United States Patent [19]

Pugh et al.

[11] Patent Number: 5,780,112
[45] Date of Patent: Jul. 14, 1998

[54] POWER-FREE LATEX ARTICLES AND METHODS OF MAKING THE SAME

[75] Inventors: Bradley L. Pugh, Midland; Russell D. Culp, Dothan, both of Ala.

[73] Assignee: LRC Products, Ltd., Broxbourne, United Kingdom

[21] Appl. No.: 645,639

[22] Filed: May 15, 1996

[51] Int. Cl.$^6$ ......................................................... B05D 3/02
[52] U.S. Cl. ..................... 427/393.3; 427/2.1; 427/340; 427/384; 427/385.5; 2/161.7; 428/36.9; 428/36.91
[58] Field of Search ........................... 427/2.1, 2.24, 427/2.25, 2.28, 2.3, 340, 384, 385.5, 393.5; 2/161.7; 428/36.9, 36.91

[56] References Cited

U.S. PATENT DOCUMENTS

| | | | |
|---|---|---|---|
| 4,575,476 | 3/1986 | Podell et al. | 428/494 |
| 4,589,873 | 5/1986 | Schwartz et al. | 604/265 |
| 4,597,108 | 7/1986 | Momose | 2/168 |
| 4,851,266 | 7/1989 | Momose et al. | 427/353 |
| 4,961,954 | 10/1990 | Goldberg et al. | 427/2 |
| 5,344,201 | 9/1994 | Gagnon et al. | 428/304.4 |
| 5,567,760 | 10/1996 | Walther et al. | 524/505 |
| 5,571,567 | 11/1996 | Shah | 427/379 |

FOREIGN PATENT DOCUMENTS

A2 0 594 410  10/1993  European Pat. Off. .

OTHER PUBLICATIONS

Pendle et al., *Dipping with Natural Rubber Latex*, NR Technical Bulletin, The Malaysian Rubber Producers' Research Association (1990).

*Primary Examiner*—José G. Dees
*Assistant Examiner*—Michael A. Williamson
*Attorney, Agent, or Firm*—Needle & Rosenberg, P.C.

[57] ABSTRACT

A method of making a latex article, by contacting a latex article with water, an aqueous emulsion comprising a high-density, substantially linear hydrocarbon polymer, and an acid-activated oxidizing agent or initiator, mixing in an acid to the reaction mixture to activate the oxidizing agent or initiator, then, after a first selected period of time sufficient to adhere the polymer to the surface of the article, mixing a stopping agent into the activated reaction mixture to substantially reduce or halt the oxidization and, after a second selected period of time sufficient to reduce substantially or halt oxidization, neutralizing the article with a neutralization mixture comprising water and a base. A method of making a latex article by contacting a latex article with a reaction mixture of water and an aqueous emulsion comprising a high-density, substantially linear hydrocarbon polymer, admixing an oxidizing agent to the reaction mixture to produce an activated reaction mixture, admixing a stopping agent to the activated reaction mixture to halt the oxidization and produce a stopped reaction mixture, and recovering the glove. A latex glove having a surface having a high-density, substantially linear polymer adhered thereto, where the glove has an average tensile strength of at least 2,500 psi.

36 Claims, No Drawings

POWER-FREE LATEX ARTICLES AND METHODS OF MAKING THE SAME

BACKGROUND OF THE INVENTION

1. Field of the Invention

This invention relates to latex articles and methods of making the same. In particular, the present invention provides improved powder-free latex gloves and methods for making such gloves, whereby the end product overcomes the natural tackiness of latex and the natural friction of the rubber surface.

2. Background

The majority of latex rubber gloves are powdered to accomplish two objectives: (1) to overcome the natural tackiness of the rubber and allow the gloves to be made without the opposite surface sticking together; and (2) to facilitate donning by overcoming the natural friction of the rubber surface against the hand. However, powder is inconvenient and can contaminate hands and clothing. Also, the powder can interfere with test results when the gloves are worn by technicians performing medical and industrial test procedures. Further, to sensitive individuals, the powders used can be hand irritants. Because powders absorb some of the naturally occurring proteins from the latex and can release these proteins into the air, they can also cause anaphylactic reactions in very sensitive individuals.

Many attempts have been made to produce powder-free, yet easily usable latex gloves. One method used to produce such gloves is to chemically treat the gloves with a solution containing free halogen (chlorine, bromine or fluorine) (see Pendle, TD and Gorton, ADT, "Dipping with natural rubber latex," NR technical bulletin, The Malaysian Rubber Producers' Research Association, Hertford, England (1980), the contents of which are incorporated fully herein by this reference). The halogen reacts with the latex surface, substituting a hydrogen atom on the rubber molecule (polyisoprene) with the halogen. This causes the surface to become more dense and harder, which in turn reduces the natural tackiness and friction, allowing the glove to be donned without additional powder. Typically, the halogen is applied either while the gloves are on the dipping form or mold or after the semi-cured glove has been removed from the dipping form or mold. The halogen is either introduced directly into the aqueous treating solution or may be generated by the dissolution of a halogen-containing solution (e.g., sodium hypochlorite) into water, with the subsequent addition of acid (e.g., HCl) to release the free halogen into the solution.

Other methods have entailed coating the latex surface with another polymer (e.g., hydrogel or polyurethane) which imparts a lower coefficient of friction to the surface.

It is, therefore, highly desirable to produce a substantially if not totally powder-free article, such as a rubber glove, that overcomes the natural tackiness of the rubber and, in the case of gloves, condoms, etc. facilitates donning by overcoming the natural friction of the rubber surface against human skin. It is also highly desirable to provide a method of treating latex articles that avoids the necessity of turning articles inside-out during treatment. Moreover, it is highly desirable to provide a processing method that does not contain contaminants. In addition, it is highly desirable to provide a method of treating a latex article, such as a glove, that produces an article that overcomes the natural tackiness of the rubber and, for donnable articles, facilitates donning without releasing powders or other substances that can irritate sensitive individuals.

SUMMARY OF THE INVENTION

The present invention fulfills these needs by providing a method of making a latex article, comprising contacting a latex article having a surface with a reaction mixture comprising effective amounts of water, an aqueous emulsion comprising a high-density, substantially linear hydrocarbon polymer, and an acid-activated oxidizing agent or initiator, admixing an effective amount of an acid to the reaction mixture to activate the oxidizing agent or initiator, thereby forming an activated reaction mixture, after a first selected period of time sufficient to adhere the polymer to the surface of the article, admixing a stoichiometrically effective amount of a stopping agent to the activated reaction mixture sufficient to substantially reduce or halt the oxidization, thereby forming a stopped reaction mixture, and after a second selected period of time sufficient to reduce substantially or halt oxidization, neutralizing the article by contacting the article with a neutralization mixture comprising water and a base.

In an alternate embodiment, the present invention provides a method of making a latex article, comprising contacting a latex article with a reaction mixture comprising effective amounts of water and an aqueous emulsion comprising a high-density, substantially linear hydrocarbon polymer, admixing an oxidizing agent to the reaction mixture to produce an activated reaction mixture, and admixing a stopping agent to the activated reaction mixture to halt the oxidization and produce a stopped reaction mixture.

In another embodiment, the present invention provides a latex glove, comprising a latex glove having a surface wherein the surface of the glove has a high-density, substantially linear polymer adhered thereto and wherein the glove has an average tensile strength of at least 2,500 psi.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

The present invention may be understood more readily by reference to the following detailed description of preferred embodiments of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

As used herein, "high-density" is used to refer to a polymer having a density of greater than 0.940.

As used herein, "substantially linear" is used to refer to a polymer where only a minor portion of the carbon chain based repeating units are branched.

As used herein, "branched" is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(CH_2CH_3$, $CH_2CH_2C(CH_3)_2CH_3$, and $CH_2CH_2C(CH_3)_3$ would all be considered branched moieties. Moreover, it is intended that "branched" variations of the moieties herein described refer to variations which do not change the basic and novel utility of the underlying compounds, products or compositions of the present invention. "Unbranched" refers to a structure where the subject carbon chain does not have any branches thereon, i.e., where the carbon chain extends in a direct line.

As used herein, "outer surface" and "inner surface" are used to refer to the portions of the glove which upon completion of manufacture and when donned are, respectively, in contact with the environment (outer surface) or in contact with the user's hands (inner surface). The term "surface", where unmodified, is meant to refer to the portion of the article in contact with the atmosphere or environment.

As used herein, a "stoichiometrically effective" amount or a "stoichiometric" amount is used to refer to an appropriate amount of the specified reagent or ingredient such that the reaction of concern is substantially completed by exhaustion of other reactants and the specified reagent or ingredient.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution. Moreover, an "optional" step in a process is a step which may or may not be necessary.

As used herein, "penetration hardness" refers to the value which results from application of ASTM protocol D1321-86 to the article being tested. For the purposes discussed herein, penetration hardness values are preferably below 2.0.

As used herein, "acid number" refers to the number of milligrams of KOH which are required to neutralize 1 gram of the compound or composition being tested, as specified in ASTM protocol D1386.

As used herein, "admix" or "admixing" refers to the contacting, optionally in liquid media, of one or more ingredients.

As used herein, "agitate" or "agitating" refers to the movement of the specified article or other item sufficient for the desired purpose. For instance, agitation of a solution may occur via the use of a stirring rod. In addition, agitation of larger batches of, e.g., gloves in a reaction vessel may be accomplished by continuously or intermittently tumbling the vessel containing the gloves. One of ordinary skill in the art would readily be able to devise other means for and methods of agitating an article or solution without undue experimentation.

As used herein, the term "partially-cured" is used to refer to latex that has not been fully or totally cured by exposure to air and heat. Partially-cured latex generally is determined based upon analysis of tensile strength. Therefore, partially-cured latex often has a tensile strength ranging from about 1500 to about 2500 psi, while totally or fully cured latex has a tensile strength of from about 3000 to about 5000 psi.

With these definitions in mind, the present invention provides a method of making a latex article, comprising contacting a latex article having a surface with a reaction mixture comprising effective amounts of water, an aqueous emulsion comprising a high-density, substantially linear hydrocarbon polymer, and an acid-activated oxidizing agent or initiator, admixing an effective amount of an acid to the reaction mixture to activate the oxidizing agent or initiator, thereby forming an activated reaction mixture, after a first selected period of time sufficient to adhere the polymer to the surface of the article, admixing a stoichiometrically effective amount of a stopping agent to the activated reaction mixture sufficient to substantially reduce or halt the oxidization, thereby forming a stopped reaction mixture, and after a second selected period of time sufficient to reduce substantially or halt oxidization, neutralizing the article by contacting the article with a neutralization mixture comprising water and a base. In a further embodiment, the present invention provides this method further comprising recovering the article.

Moreover, in an alternate embodiment, the article has inner and outer surfaces and further comprising, between the contacting and the first admixing step, in a first agitating step, agitating the reaction mixture for a third selected amount of time whereby the reaction mixture is thoroughly dispersed over the inner and outer surfaces of the article. Therefore, the agitating step ensures that the polymer is thoroughly dispersed through the articles, and in particular, for latex gloves, is dispersed both inside and outside of the latex gloves. In a further embodiment, the first agitation step occurs for from about 10 to about 30 minutes.

In yet another embodiment, the present invention provides a method further comprising, between the first and second admixing steps, in a second agitating step, agitating the reaction mixture with the acid for a fourth selected amount of time whereby the activated reaction mixture is thoroughly dispersed over the inner and outer surfaces of the article. In a further embodiment, the second agitation step is accomplished by tumbling. The second agitation step in the presence of the acid ensures that the polymer adheres to the surface of the latex article. In another embodiment, the second agitation step occurs for from about 10 to about 20 minutes.

In yet another preferred embodiment, the acid-activated oxidizing agent is a halogen-containing salt. In a further preferred embodiment, the acid-activated oxidizing agent is a hypochlorite.

In yet a further preferred embodiment, the high-density, substantially linear hydrocarbon polymer comprises polyethylene. In yet another embodiment, the polyethylene comprises at least 60% by weight of the emulsion, wherein the emulsion further comprises polypropylene, polymethylene, paraffin, low density polyethylene, or a mixture thereof. One of ordinary skill in the art would recognize that the emulsion could contain other ingredients without altering the basic and novel utility of the present invention.

In yet a further embodiment, the ratio of the components in the reaction mixture comprise, for each 1.0 part by weight of the article, from about 5.5 to about 15.0 parts by weight water, from about 0.2 to about 1.0 parts by weight acid-activated oxidizing agent comprised of hypochlorite solution (BLC100, Sodium Hypochlorite Solution 7–16%, Vertex Chemical Corp., St. Louis, Mo.) containing from about 10 to about 15% available chlorine, from about 0.8 to about 1.4 parts by weight of polymer comprised of an about 35% polyethylene emulsion, and from about 0.10 to about 0.20 parts by weight of acid. Moreover, in another embodiment, the present invention provides the above-described method wherein the ratio of the components in the reaction mixture comprise, for each 1.0 part by weight of the article, about 11.0 parts by weight water, about 0.60 parts by weight acid-activated oxidizing agent comprised of hypochlorite solution containing from about 10 to about 15% available chlorine, about 1.1 parts by weight of polymer comprised of an about 35% polyethylene emulsion, and about 0.16 parts by weight of acid.

In a further embodiment, the acid is sulfuric acid or hydrochloric acid. In a further embodiment, the acid is 15% concentration hydrochloric acid and comprises from about 0.10 to about 0.50 parts of the activated reaction mixture. In yet a further preferred embodiment, the hydrochloric acid comprises about 0.20 parts of the activated reaction mixture.

In another embodiment, the present invention provides the method as described above further comprising, before the contacting step, agitating the article in slurry of a starch, calcium carbonate, a detackifying agent, or a mixture thereof.

In an alternate embodiment, the present invention provides a method further comprising, before the contacting step, stripping the article, from its mold or form, using at least one pressurized water source.

In a further embodiment, the stopping agent is an alkaline hydroxide. In a preferred embodiment, the stopping agent is sodium hydroxide. In yet a further preferred embodiment, the sodium hydroxide comprises from about 0.010 to about 0.0625 parts by weight of the stopped reaction mixture. In yet a further preferred embodiment, the sodium hydroxide comprises about 0.0325 parts by weight of the stopped reaction mixture.

In an alternate embodiment, the neutralization mixture comprises from about 5.3 to about 15.0 parts of water and from about 0.025 to about 0.0625 parts of sodium hydroxide. In a further embodiment, the present invention provides a method further comprising, after the neutralizing step, rinsing the article one or more times with water.

In an alternative embodiment, the base is sodium hydroxide, potassium hydroxide or ammonium hydroxide. In a preferred embodiment, the base is sodium hydroxide.

In a preferred embodiment, the article is a glove.

In an alternate embodiment, the present invention provides a method of making a latex article, comprising contacting a latex article with a reaction mixture comprising effective amounts of water and an aqueous emulsion comprising a high-density, substantially linear hydrocarbon polymer, admixing an oxidizing agent to the reaction mixture to produce an activated reaction mixture, and admixing a stopping agent to the activated reaction mixture to halt the oxidization and produce a stopped reaction mixture. In a further embodiment, the present invention provides the above method further comprising recovering the article. In yet another embodiment, the oxidizing agent is a halogen. In a further embodiment, the oxidizing agent is chlorine or bromine.

In another embodiment, the present invention provides the above described method, wherein the stopping agent is an alkaline hydroxide. In another embodiment, the method further comprises, in a third admixing step, admixing a neutralization agent to the stopped reaction mixture.

In addition, the present invention provides the above described method wherein the recovering step comprises rinsing the article one or more times with water and drying the article.

In an alternate embodiment, the present invention provides an article produced by the method of as described above. In a further embodiment, the article is a glove.

Finally, in yet another embodiment, the present invention provides a latex glove, comprising a latex glove having a surface wherein the surface of the glove has a high-density, substantially linear polymer adhered thereto and wherein the glove has an average tensile strength of at least 2,500 psi.

General Production Method

In one embodiment, the method used to coat a latex article, such as a rubber glove, is as follows. Latex gloves are conventionally straight-dipped in latex a multiplicity, preferably from 1 to 3 times, more preferably from 1 to 2 times, in order to build-up a sufficient thickness. For instance, if the gloves are to be used as surgical gloves, the gloves will generally have a thickness ranging from about 0.08 mm to about 0.25 mm. However, it should be emphasized, and one of ordinary skill in the art would recognize, that the method could be used on gloves produced by methods other than straight-dipping, such as, but not limited to, coagulant dipping and heat-sensitive dipping.

In general, for a straight-dipping process, approximately 0.03 to about 0.04 mm of latex are deposited for each dipping. One of skill in the art would recognize, however, that more dippings could be used to increase the thickness of the article, the selected number of dippings depending upon the desired application of the glove or article. Nevertheless, in a preferably embodiment, the gloves are then partially-cured by air and heat (i.e. the tensile strength ranges from about 1500 to about 2500 psi, as opposed to about 3000 to about 5000 psi for totally cured latex) on the production line and then stripped from their molds. However, it is to be understood that the methods of the present invention would also be operative on fully or totally cured latex articles. Stripping is preferably accomplished by using high pressure water jets.

In a preferable embodiment, powder or powder-containing slurries are not used. Since no powder release agents are used in the straight-dipping process, the stripped wetted gloves are non-powdered at this stage. Optionally, however, a powder or powder-containing slurry, such as, but not limited to, a starch/calcium carbonate slurry as described herein, could be used.

The wetted, stripped gloves are then placed into a reaction vessel. Such vessels are typically capable of containing 13,000–15,000 gloves. However, one of ordinary skill in the art would be able to scale the vessel and all of the details of the method to suit their particular purpose.

The following proportions of gloves and chemicals are then introduced into the reaction vessel as described below:

| Material | Ratio (preferred) | Ratio by Weight (Range) |
|---|---|---|
| Gloves | 1.0 | 1.0 |
| Water | 11.0 | 5.5–15.0 |
| Oxidization Source* | 0.60 | 0.2–1.0 |
| Polyethylene Emulsion | 1.1 | 0.8–1.4 |

*10–15% available oxidizer

In a preferred embodiment, the order of introduction is as follows. The gloves are first placed within the vessel. Then the water and polymer emulsion are added. Next the oxidizer, such as, but not limited to hypochlorite or another suitable halogen source, is added. Sodium or calcium hypochlorite is preferred for the oxidizing hypochlorite solution, but other halogen-releasing compounds or oxidizing agents could also be used instead of hypochlorite. In particular, chlorine or bromine could also be used.

The vessel containing these ingredients is agitated in order to fully disperse the reactants in the vessel about the surfaces of the articles.

The polyethylene emulsion used in the preferred embodiment is a 30% to 35% by weight in water emulsion of polyethylene (ChemCor Poly Emulsion 325N35, Chemical Corporation of America, Chester, N.Y.). This emulsion may be diluted with water to form an about 11 to about 14% high-density linear polyethylene emulsion that is preferable for ease of use for practicing the present invention. However, it should be noted that the above-listed ratios determine the preferable amounts of polyethylene in the reaction vessel, regardless of the actual formulation used.

In one embodiment, the polyethylene has a melting point of from about 110° C. to about 150° C., preferably from about 120° C. to about 125° C. Moreover, in another embodiment, the polyethylene has a penetration hardness of less than about 2.0 decimillimeter, preferably of from 0.8 to about 1.0 decimillimeter.

In addition, in another embodiment, the polyethylene has a density of from about 0.940 to about 1.050, preferably about 0.960. Also, in yet another embodiment, the polyethylene has an acid number of from at least about 15 to about 40, preferably from about 25 to about 27.

A wetting agent is optionally used to stabilize the emulsion of the hydrophobic polyethylene and also facilitates entry of the reactants into the glove, allowing the inner surface, especially toward the fingertips to receive treatment without having to turn the gloves inside out. It is preferred that the wetting agent have an HLB (hydrophile/lipophile balance, where higher values indicate more water solubility and lower values indicate more oil solubility) value of from 5 to about 20, preferably of from 10 to about 12. If the wetting agent is sufficiently powerful, no additional reaction facilitators are required. However, if a less powerful wetting agent is used, the stripped, partially-cured gloves optionally may be treated with a starch/calcium carbonate slurry (as described elsewhere herein) or other detackifying agent and then dried. If a slurry is added, the powder, along with the any other unreacted components of the mixture, are removed during the final washing of the gloves resulting in a powder-free (i.e., the final product does not require a powder to prevent tackiness or to aid in donning the product) glove. Other suitable facilitators include all known to those of skill in the art, including, but not limited to, starch/$CaCO_3$ slurry, sodium carbonate, sodium hydroxide, sodium bicarbonate, and other low foaming surfactants (e.g., SPOT GUARD®, U.S. Chemical, Watertown, Wis.) and detackifying agents.

As used herein, the starch/calcium carbonate ($CaCO_3$) slurry is comprised of the following ingredients (in wt. %): starch 0.6% (Hubinger Co., Keokuk, Iowa), calcium carbonate 4.0% (Van Waters & Rogers, Inc., Kirkland, Wash.), emulsified silicone (as a 35% in water emulsion (SM2128 Silicon Emulsion, GE Silicones, Waterford, N.Y.)), polyether wetting agent 0.5%, bactericide (dimethoxane) (GIVGARD DXN®, Givaudan-Roule, Clifton, N.J.) with the remainder being water.

Following introduction of the gloves and reactants to the vessel, the vessel is tumbled, rotated, or otherwise agitated for from about 10 to about 60 minutes to permit mixing of the reaction solution throughout the inner and outer surfaces of the gloves.

Acid is then added, preferably slowly, to the reaction vessel (containing the gloves, water, halogen source, and polymer emulsion) in the ratio by weight of gloves of 0.10–0.80, more preferably 0.10 to about 0.20, even more preferably 0.16. Typically, 15% hydrochloric acid (HCl) is used. Nonetheless, the acid is added in a sufficient amount to lower the pH of the solution to from about 2.0 to about 5.0, preferably from pH 4.0 to pH 5.0. The amount of acid may either be predetermined or may be determined by assaying the pH of the solution as the acid is added. Although HCl is preferred, other acids, such as sulfuric acid ($H_2SO_4$), acetic acid or other mineral acids may be used. Preferably, the acid only releases free chlorine from the hypochlorite solution when the appropriately low (<5.0) pH is achieved.

After introduction of the acid into the reaction vessel, further agitation is carried out for from about 10 to about 20 minutes to allow sufficient time for the acid to react with the other chemicals and for corresponding reaction products (e.g., the released oxidizer) to chemically react with the latex surfaces of the gloves thereby adhering the polymer to the surfaces.

Without wishing to be bound by theory, during this in situ reaction, it is believed that the acid liberates free halogen (e.g., chlorine). The released halogen, in turn, reacts with both the glove surface and the linear polyethylene to remove or substitute for hydrogen atoms. When a halogen reacts with one end of the linear polyethylene chain, the chain is then capable of bonding directly to the isoprene molecule on the surface of the glove.

It is believed that the halogen is a catalyst for bonding between the polyethylene and the latex (isoprene) molecules. If the polyethylene is physically coated onto the rubber surface as in other known methods, the polyethylene and isoprene generally do not chemically bond each other and, therefore, the polyethylene can flake off when the finished glove product is stretched. However, in accordance with the present invention, when the polyethylene is chemically bonded or otherwise adhered to the glove surface, flaking off or other removal is impossible without destruction of the latex glove itself. In addition, some chlorine-to-rubber bonding also occurs via a further substitution or addition reaction. It is believed that this chlorine-to-rubber bonding accounts for a less tacky final latex product.

After the reactions in the vessel have proceeded to the desired point, the reaction is stopped or substantially reduced by the addition of a stoichiometric amount of a sodium hydroxide solution (caustic soda). One of skill in the art would recognize that other bases could be used to stop the oxidization reaction, such as, but not limited to, KOH, $NH_4OH$ or any other suitable hydroxylated base or alkaline hydroxide. In a preferred embodiment, a ratio of from about 0.0010 to about 0.625, preferably 0.0325 of NaOH (caustic soda) (CSD250, Industrial Chemicals Inc., Birmingham, Ala.) is used. Thereafter, agitation is resumed for an additional about 10 to about 60 minutes, preferably about 30 minutes. After this agitation, the contents of the vessel are drained.

After draining is substantially completed, a neutralization rinse is initiated. In one embodiment, the neutralization rinse uses a neutralizing agent which is comprised of water at a ratio of from about 5.3 to about 15.0, preferably about 11.0 with an addition of NaOH at a ratio of from about 0.025 to about 0.0625, preferably about 0.0325. The vessel with the gloves and the neutralization rinse is then further agitated for from about 10 to about 120, preferably about 50 additional minutes. After neutralization has been completed, the gloves are rinsed with water one or more times, preferably two times, at a ratio (water to gloves) of from about 5.3 to about 15.0, preferably 11.0.

After rinsing with water, the gloves are dried using a dryer configured to uniformly dry the gloves by controlling the temperature of the incoming heated air by monitoring the exhaust temperature and using the exhaust temperature to control the temperature of the incoming heated air. The gloves may optionally be air dried.

Since the polyethylene emulsion penetrates inside the gloves during processing in the reaction vessel, further processing (e.g., turning) is not required to place the treated surface inside the glove).

Other embodiments are possible in which acid is not required. It is believed that the acid helps to release chlorine from the hypochlorite. Therefore, for example, if elemental chlorine or another strong gaseous oxidizing agent is bubbled through the mixture of gloves, water, and polyethylene emulsion, the chlorine, other halogen or oxidizing agent would not require the acid to be released. However, it is important that the oxidizing agent be introduced after the mixture has been agitated to distribute the polyethylene over the inner and outer surfaces of the gloves. Otherwise, some portion of the glove surfaces may undergo only the displacement or addition reaction with the oxidizing agent. Even where an acid is not used, the stopping and neutralization steps of the present invention are expected to provide superior results.

The preferred embodiments of the above-described latex articles and methods for making such articles are set forth in the following examples. Other features of the invention will become apparent from the following examples, which are for illustrative purposes only and are not intended as a limitation upon the present invention.

EXAMPLE I

The method of the invention was used to coat latex gloves as follows. Latex gloves were conventionally straight-dipped. The gloves were then partially-cured by air and heat on the production line and stripped from their molds using high pressure water jets.

The wetted, stripped gloves were placed into a reaction vessel capable containing 13,000–15,000 gloves. Into the reaction vessel were added the following proportions of other chemicals in addition to the gloves:

| Material | Ratio (preferred) | Ratio by Weight (Range) |
| --- | --- | --- |
| Gloves | 1.0 | 1.0 |
| Water | 11.0 | 5.5–15.0 |
| Hypochlorite Solution* | 0.60 | 0.2–1.0 |
| Polyethylene Emulsion (30–35%) | 1.1 | 0.8–1.4 |

*10–15% available chlorine

In particular, after the gloves were placed into the vessel, the water and polymer emulsion were added. Next the hypochlorite was added. The vessel containing these ingredients was agitated.

The polyethylene emulsion used was a 35% by weight in water emulsion of polyethylene (ChemCor High Density Polyethylene Emulsion, Chemical Corporation of America, Chester, N.Y.).

Following introduction of the gloves and reactants to the vessel, the vessel was tumbled for about 30 minutes to permit mixing of the reaction solution over the surfaces of the gloves.

Hydrochloric acid (15%) was then added, slowly, to the reaction vessel in a ratio by weight of gloves of 0.16, i.e., such that enough of the HCl was added to lower the pH of the solution to between 4.0 and 5.0. After the acid was added into the reaction vessel, a further agitation was carried out for 10 minutes.

Next, the reaction was stopped by addition of a stoichiometric amount of a sodium hydroxide solution, i.e., a weight ratio of about 0.0325 of NaOH. Thereafter, agitation was resumed for an additional 30 minutes. After this agitation, the contents of the vessel were drained.

After draining, a neutralization rinse was initiated. The neutralization rinse used a neutralizing agent made of water at a ratio of 11.0 with an addition of NaOH at a ratio of 0.0325. The vessel with the gloves and the neutralization rinse was then further agitated for 50 minutes. After neutralization was completed, the gloves were rinsed with water two times at a ratio (water to gloves) of 11.0. The gloves were then dried using a dryer.

In tests conducted on the gloves produced by the above-described method, in comparison to those produced with the standard halogenation process (see Pendle, TD and Gorton, ADT, "Dipping with natural rubber latex," NR technical bulletin, The Malaysian Rubber Producers' Research Association, Hertford, England (1980), the contents of which are incorporated fully herein by this reference), a number of differences were observed. First, gloves produced by the method of this Example have lower friction and are more-easily donned. The method of this Example applies a softer, more supple, feel to the gloves than does a standard halogenation process, which tends to stiffen the feel of the gloves. Also, residual surface particulate levels are much lower on the gloves produced by the method of this Example, reducing contamination of hands and clothing and the potential for interference with test results when the gloves are worn by technicians performing medical and industrial test procedures.

The cytotoxicity of the end-product has been found to be dramatically lowered by the new method. This indicates that skin irritation potential should be lessened. Residual proteins (as tested by the Bradford method) are lower on the gloves of the present invention compared to either standard powdered gloves or standard halogenated gloves. The results also indicate a lessened potential for skin irritation or anaphylactic reactions which have been associated with residual protein levels in latex gloves. RAST Inhibition testing confirmed that the total allergen levels on gloves produced by the method in Example I are very low.

Photomicrographs revealed the surface topography of the gloves both before and after stretching was substantially altered over both powdered and halogenated gloves. Without wishing to be bound by theory, this change in topography is likely due to the polyethylene bonding at the surface and is the reason for improved donnability, feel, and particulate levels. The polyethylene appears to chemically graft or adhere onto the surface of the rubber. Unlike coatings which can flake off when the glove is stretched, the polyethylene bonded in accordance with the present invention cannot be removed.

Polyethylene coating was confirmed by FTIR scan— infrared of a hot toluene surface rinse.

EXAMPLE II

The method of the invention improves color stability of the glove because it prevents residual chlorine from destabilizing the product over time. Moreover, the use of a caustic neutralization step serves to remove further undesirable by-products from the polymer coated latex article. For instance, gloves produced in accordance with Example I were assayed against gloves produced by a similar process to that described for Example I, but without the specified stopping or neutralization steps. In particular, the control gloves were produced by a process during which thiosulfate was used to reduce further oxidation and no neutralization step was used.

The method of Example I also reduced carbon disulfide and decane-3 methyl by-products relevant to improved colored gloves. In addition, the presence of these chemicals is believed to account for the pungent odor and significant discoloration noted for gloves produced by the process not including the specified stopping or neutralization steps.

EXAMPLE III

Gloves or other latex articles produced in accordance with the method described in Example I provided surprisingly improved properties, such as tensile strength. In particular, gloves produced by the method of the invention reduce the opportunity for residual chlorine to continue to react with the rubber surface thereby lowering tensile strength. To demonstrate this feature, the following test was conducted. Gloves produced as in Example I and gloves produced by the process not including the specified stopping or neutralization steps were aged at 70° C. for 7 days. The gloves of Example I showed tensile strengths of from 2500 to 3000 psi, while the gloves produced by the process not including specified stopping or neutralization steps showed tensile strengths of only from 2000 to 2300 psi.

Similarly, gloves produced by a process which does not include the specified stopping and neutralization steps tended to develop a pungent acidic odor when exposed to heat during aging. Without wishing to be bound by theory, it is believed that because the method of the present invention reduces the opportunity for residual chlorine to continue reacting with the rubber surface, that the method of the invention does not suffer from this problem.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of making a latex article, comprising:
    a.) contacting a latex article having a surface with a reaction mixture comprising effective amounts of
        i) water,
        ii) an aqueous emulsion comprising a high-density, substantially linear hydrocarbon polymer, and
        iii) an acid-activated oxidizing agent or initiator;
    b.) in a first admixing step, admixing an effective amount of an acid to the reaction mixture to activate the oxidizing agent or initiator, thereby forming an activated reaction mixture;
    c.) after a first selected period of time sufficient to adhere the polymer to the surface of the article, in a second admixing step, admixing a stoichiometrically effective amount of a stopping agent to the activated reaction mixture sufficient to substantially reduce or halt the oxidization, thereby forming a stopped reaction mixture; and
    d.) after a second selected period of time sufficient to reduce substantially or halt oxidization, neutralizing the article by contacting the article with a neutralization mixture comprising water and a base.

2. The method of claim 1, further comprising recovering the article.

3. The method of claim 1, wherein the article has inner and outer surfaces and further comprising, between the contacting and first admixing steps, in a first agitating step, agitating the reaction mixture for a third selected amount of time whereby the reaction mixture is thoroughly dispersed over the inner and outer surfaces of the article.

4. The method of claim 3, further comprising, between steps first and second admixing steps, in a second agitating step, agitating the reaction mixture with the acid for a fourth selected amount of time whereby the activated reaction mixture is thoroughly dispersed over the inner and outer surfaces of the article.

5. The method of claim 4, wherein the second agitation step is accomplished by tumbling.

6. The method of claim 1, wherein the acid-activated oxidizing agent is a halogen-containing salt.

7. The method of claim 1, wherein the acid-activated oxidizing agent is a hypochlorite.

8. The method of claim 1, wherein the high-density, substantially linear hydrocarbon polymer comprises polyethylene.

9. The method of claim 8, wherein the high-density, substantially linear hydrocarbon polymer comprises at least 60% by weight of the emulsion, wherein the emulsion further comprises polypropylene, polymethylene, paraffin, low density polyethylene, or a mixture thereof.

10. The method of claim 1, wherein the ratio of the components in the reaction mixture comprises, for each 1.0 part by weight of the article, from 5.5 to 15.0 parts by weight water, from 0.2 to 1.0 parts by weight acid-activated oxidizing agent comprised of hypochlorite solution containing from 10 to 15% available chlorine, from 0.8 to 1.4 parts by weight of polymer comprised of a 35% polyethylene emulsion, and from 0.10 to 0.20 parts by weight of acid.

11. The method of claim 1, wherein the ratio of the components in the reaction mixture comprises, for each 1.0 part by weight of the article, 11.0 parts by weight water, 0.60 parts by weight acid-activated oxidizing agent comprised of hypochlorite solution containing from 10 to 15% available chlorine, 1.1 parts by weight of polymer comprised of a 35% polyethylene emulsion, and 0.16 parts by weight of acid.

12. The method of claim 3, wherein the first agitation step occurs for from 10 to 30 minutes.

13. The method of claim 4, wherein the second agitation step occurs for from 10 to 20 minutes.

14. The method of claim 1, wherein the acid is sulfuric acid or hydrochloric acid.

15. The method of claim 1, wherein the acid is 15% concentration hydrochloric acid and comprises from 0.10 to 0.50 parts of the activated reaction mixture.

16. The method of claim 15, wherein the hydrochloric acid comprises 0.20 parts of the activated reaction mixture.

17. The method of claim 1, further comprising, before the contacting step, agitating the article in slurry of a starch, calcium carbonate, a detackifying agent, or a mixture thereof.

18. The method of claim 1, further comprising, before the contacting step, stripping the article from a mold using at least one pressurized water source.

19. The method of claim 1, wherein the stopping agent is an alkaline hydroxide.

20. The method of claim 1, wherein the stopping agent is sodium hydroxide.

21. The method of claim 20, wherein the sodium hydroxide comprises from 0.010 to 0.0625 parts by weight of the stopped reaction mixture.

22. The method of claim 20, wherein the sodium hydroxide comprises 0.0325 parts by weight of the stopped reaction mixture.

23. The method of claim 1, wherein the neutralization mixture comprises from 5.3 to 15.0 parts of water and from 0.025 to 0.0625 parts of sodium hydroxide.

24. The method of claim 23, further comprising, after the neutralizing step, rinsing the article one or more times with water.

25. The method of claim 1, wherein the base is sodium hydroxide, potassium hydroxide or ammonium hydroxide.

26. The method of claim 1, wherein the base is sodium hydroxide.

27. The method of claim 1, wherein the article is a glove.

28. A method of making a latex article, comprising:
   a.) contacting a latex article with a reaction mixture comprising effective amounts of
      i) water, and
      ii) an aqueous emulsion comprising a high-density, substantially linear hydrocarbon polymer;
   b.) in a first admixing step, admixing an oxidizing agent to the reaction mixture to produce an activated reaction mixture; and
   c.) in a second admixing step, admixing a stopping agent to the activated reaction mixture to halt the oxidization and produce a stopped reaction mixture.

29. The method of claim 28, further comprising recovering the article.

30. The method of claim 28, wherein the oxidizing agent is a halogen.

31. The method of claim 28, wherein the oxidizing agent is chlorine.

32. The method of claim 28, wherein the oxidizing agent is bromine.

33. The method of claim 28, wherein the article is a glove.

34. The method of claim 2, wherein the recovering step comprises:
   a.) rinsing the article one or more times with water; and
   b.) drying the article.

35. The method of claim 28, wherein the stopping agent is an alkaline hydroxide.

36. The method of claim 28, further comprising, in a third admixing step, admixing a neutralization agent to the stopped reaction mixture.

* * * * *

UNITED STATES PATENT AND TRADEMARK OFFICE
CERTIFICATE OF CORRECTION

PATENT NO. : 5,780,112
DATED : July 14, 1998
INVENTOR(S) : Bradley L. Pugh and Russell D. Culp It is certified that error appears in the above-identified patent and that said Letters Patent is hereby corrected as shown below:

On the title page: Item [54] and Column 1, line 1, replace "Power-free" with --Powder-free--.
Column 3, line 45: Replace "D1386" with --D1321-86--.
Column 8, line 32: Replace "bond each" with --bond with each--.

Signed and Sealed this

Fifteenth Day of December, 1998

*Attest:*

BRUCE LEHMAN

*Attesting Officer*  *Commissioner of Patents and Trademarks*